(12) United States Patent
Yokoyama (10) Patent No.: US 8,673,648 B2
(45) Date of Patent: Mar. 18, 2014

(54) SUGAR ANALYSIS DEVICE AND ANALYSIS METHOD

(75) Inventor: Tetsuo Yokoyama, Ashiya (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 0 days.

(21) Appl. No.: 13/643,308

(22) PCT Filed: Apr. 25, 2011

(86) PCT No.: PCT/JP2011/060040
§ 371 (c)(1),
(2), (4) Date: Jan. 2, 2013

(87) PCT Pub. No.: WO2011/136165
PCT Pub. Date: Nov. 3, 2011

(65) Prior Publication Data
US 2013/0095570 A1    Apr. 18, 2013

(30) Foreign Application Priority Data
Apr. 28, 2010    (JP) .................. 2010-104324

(51) Int. Cl.
*G01N 30/96* (2006.01)
*G01N 30/00* (2006.01)

(52) U.S. Cl.
USPC .............. 436/94; 436/93; 436/91; 422/82.08; 422/82.05; 422/68.1; 422/50

(58) Field of Classification Search
USPC ............. 436/94, 95, 161, 171, 172; 73/61.52, 73/61.55, 61.56; 422/82.08, 82.05, 68.1, 422/50
See application file for complete search history.

(56) References Cited

U.S. PATENT DOCUMENTS

| 6,855,555 B2 | 2/2005 | Kakita et al. |
| 2003/0129761 A1 | 7/2003 | Kakita et al. |

FOREIGN PATENT DOCUMENTS

| JP | 59 111059 | 6/1984 |
| JP | 2002 131326 | 5/2002 |
| JP | 2003 194791 | 7/2003 |
| JP | 2007 120972 | 5/2007 |
| JP | 2009 036685 | 2/2009 |

OTHER PUBLICATIONS

S. Sawada et al., "Determination of Sugar Phosphates and Nucleotides Related to Photosynthesis Metabolism by High-Performance Anion-Exchange Liquid Chromatography with Fluorometric and Ultraviolet Detection," Analytical Biochemistry, vol. 314 (2003) pp. 63-69.*

Funakoshi Yakuhin KK, "Reagent for high performance liquid chromatography and preparation thereof," Patent Abstracts of Japan, Publication Date: Jun. 27, 1984; English Abstract of JP-59-111059.

(Continued)

*Primary Examiner* — Christine T Mui
(74) *Attorney, Agent, or Firm* — Millen, White, Zelano & Branigan, P.C.

(57) ABSTRACT

Disclosed is a method separation analysis of reducing sugars with enhanced sensitivity and an analytical apparatus therefore employing the post-column fluorescence detection/boric acid complex anion exchange method. The method disclosed is a method for analysis of reducing sugars using the post-column fluorescence detection/boric acid complex anion exchange method, and characterized in that a back-pressure generator is installed in the flow path between the heater, which is for causing a reaction by heating a sample separated by column chromatography with a basic amino acid, and a fluorometric detector.

6 Claims, 2 Drawing Sheets

(56) References Cited

OTHER PUBLICATIONS

International Search Report for PCT/JP2011/060040; Date of actual completion of the international search: Jul. 7, 2011; Date of mailing of the international search report: Jul. 19, 2011.
Jasco Corp., "Supercritical System," Patent Abstract of Japan, Publication Date: May 17, 2007; English Abstract of JP-2007 120972.
Mikami et al., "Post-column fluorometric detection of reducing sugars in high performance liquid chromatography using arginine," Journal of Japan Society for Analytical Chemistry, Jun. 5, 1983, vol. 32, No. 6, pp. E207-E210.

Pickering, M. V. et al., "Assembling an HPLC Postcolumn System: Practical Considerations," LC GC, Nov. 1988, vol. 6, No. 11, pp. 994, 996-997.
Shimadzu Corp., "Method of analyzing reduction sugar," Patent Abstracts of Japan, Publication Date: Feb. 19, 2009; English Abstract of JP-2009 036685.
Shimadzu Corp., "Post column reagent mixing reactor," Patent Abstracts of Japan, Publication Date: May 9, 2002; English Abstract of JP-2002 131326.

* cited by examiner

SUGAR ANALYSIS DEVICE AND ANALYSIS METHOD

TECHNICAL FIELD

The present invention relates to an apparatus for separation analysis of reducing sugars by a post-column fluorescence detection/boric acid complex anion exchange method as well as a method for separation analysis using the apparatus, and, in particular, to an apparatus for separation analysis of reducing sugars by the post-column fluorescence detection/boric acid complex anion exchange method comprising a heater for heating to cause a basic amino acid to react with a sample solution having undergone separation by column chromatography, and a back-pressure generator installed in the flow path between the heater and a fluorometric detector.

A method for analysis of reducing sugars is known which comprises subjecting a sample containing reducing sugars to liquid chromatography using as a mobile phase an aqueous solution containing boric acid to obtain an eluate, adding to the eluate, in the flow path, a boric acid aqueous solution containing a basic amino acid, such as arginine, causing a reaction to proceed by heating, then cooling the reaction solution, and irradiating the reaction solution with excitation light to measure the intensity of fluorescence or measuring absorbance (Patent Document 1). The apparatus used there comprises a liquid chromatography system with an extended flow path to which is connected a supply channel for a boric acid aqueous solution containing a basic amino acid and are attached a heater, a cooling device, an excitation light irradiator, and a device for measuring fluorescence intensity or the like. According to the method, the provision of the supply channel is indispensable in order to add a boric acid aqueous solution containing a basic amino acid to the eluate from the liquid chromatography for letting the reaction proceed.

Further, an improved type of the above method is known, in which a sample containing reducing sugars is subjected to liquid chromatography using a mobile phase containing boric acid and a basic amino acid, such as arginine, as a reagent, then eluted, and the eluate thus obtained is heated to cause the reagent and the reducing sugars to react (heat reaction) and then cooled, and this reaction mixture solution then is measured either for intensity of fluorescence emitted under irradiation with excitation light or for absorbance (Patent Document 2). In this method, as a boric acid aqueous solution containing a basic amino acid is employed as the mobile phase for liquid chromatography, there is no need for providing a supply channel for later addition of a boric acid aqueous solution containing a basic amino acid. The above methods for analysis of reducing sugars are called post-column fluorescence detection/boric acid complex anion exchange method.

In detection of reducing sugars eluted from a column, both of the above methods for analysis of reducing sugars utilize production of strong fluorogenic derivatives by the heat reaction of reducing sugars with a basic amino acid, such as arginine, in the presence of boric acid (Non-patent Document 1). These strong fluorogenic derivatives are brown-colored melanoidine, which is formed by the heat reaction (Maillard reaction) of reducing sugars with a basic amino acid (an amino compound), and emits light at the wavelength of 430 nm when irradiated with excitation light at the wavelength of 320 nm. These methods for analysis of reducing sugars utilize the properties of reducing sugars that they readily bind to boric acid to form an anionic complex ion, and that this anionic complex ion is retained in an anion exchanger column.

In the post-column fluorescence detection/boric acid complex anion exchange method, an aqueous solution (pH 7-10) is employed as a mobile phase which contains a basic amino acid at a concentration of 0.01-5% and boric acid at a concentration of 0.05-0.5 M. Those amino acids which can be employed above are arginine, lysine, histidine, and the like. Recently, it is also known to perform the analysis of sugars employing a mobile phase for liquid chromatography with a gradient formed by a 0.1 M borate buffer and a 0.4 M borate buffer (Patent Documents 3, 4).

In the post-column fluorescence detection/boric acid complex anion exchange method, elution of a sample in liquid chromatography is carried out at temperatures from room temperature to 70° C., and the heat reaction (Maillard reaction) is allowed to proceed at 140-180° C. (Patent Document 2). Since the reaction and elution have been performed at such high temperatures at high boric acid concentrations, the heat causes such phenomena as expansion of the mobile phase and convection in the mobile phase. These phenomena can cause noises in the fluorescence detected by the fluorometric detector in the post-column fluorescence detection/boric acid complex anion exchange method, and can result in the reduction of detection sensitivity. Thus, in analysis of reducing sugars by such methods, particularly in their quantitative analysis, it is required to compensate the detection result by using special software.

The reducing sugars which can be analyzed using the post-column fluorescence detection/boric acid complex anion exchange method are those which undergo the Maillard reaction with the basic amino acids, including monosaccharides such as glucose, mannose, galactose, fructose, and rhamnose; oligosaccharides such as maltose and maltotriose; amino sugars such as glucosamine, galactosamine; and uronic acids such as glucuronic acid.

Examples of analytes of this method include reducing sugars derived from sugar chains of glycoproteins. Reducing sugars which form sugar chains of glycoproteins include monosaccharides such as mannose, galactose, and fucose; amino sugars such as galactosamine. Such sugar chains sometimes contain mannose-6-phosphate (M6P).

PRIOR ART DOCUMENTS

Patent Documents

[Patent Document 1] Japanese Patent Application Publication No. S58-216953
[Patent Document 2] Japanese Patent Application Publication No. S61-25059
[Patent Document 3] Japanese Patent Application Publication No. 2006-184131
[Patent Document 4] Japanese Patent Application Publication No. 2008-425550

Non-Patent Document

[Non-patent Document 1] Mikami H. et. al., Bunseki Kagaku (1983) 32, E207

DISCLOSURE OF THE INVENTION

Technical Problem

Against the above mentioned background, a purpose of the present invention is to enhance detection sensitivity in the post-column fluorescence detection/boric acid complex anion exchange method, by eliminating noises in the fluorescence detected by a fluorometric detector which take place as a result of heating and cooling the flow path.

Means to Solve the Problem

In a study for the above-mentioned object, the inventor of the present invention attempted, in the post-column fluorescence detection/boric acid complex anion exchange method, to place a back-pressure generator in the flow path between the heater, which caused a basic amino acid to react by heat with the sample solution separated by column chromatography, and a fluorometric detector. As a result, the inventor found that the placing of the back-pressure generator can eliminate noises in the fluorescence detected by the fluorometric detector, and thereby enhance detection sensitivity. The present invention was completed on the basis of these findings.

Namely, the present invention provides as follows.

1. An apparatus for separation analysis of reducing sugars contained in a sample solution using column chromatography, comprising an anion exchange resin column for separation of reducing sugars contained in the sample solution, a heater for causing reducing sugars contained in the eluate from the column to react with a basic amino acid, a fluorometric detector for measuring the intensity of fluorescence emitted from the eluate under continuous irradiation with excitation light after the reaction in the heater, a back-pressure generator installed between the heater and the fluorometric detector.

2. The apparatus for separation analysis of reducing sugars according to 1 above, wherein a cooling device was further installed between the heater and the back-pressure generator.

3. A method for separation analysis of reducing sugars using the apparatus according to 1 or 2 above, comprising loading the sample solution containing reducing sugars on an anion exchange resin column, washing the column by passing therethrough a sufficient volume of a first mobile phase which is an aqueous solution containing boric acid at a predetermined concentration, supplying to the column continuously at a predetermined flow rate a second mobile phase which is a boric acid aqueous solution containing an elevated concentration of boric acid or water-soluble inorganic salt, as compared with the first mobile phase to elute the reducing sugars, leading the eluate from the column continuously to a flow path, continuously adding at least one basic amino acid at a predetermined rate to the eluate, letting the eluate containing the basic amino acid added thereto flow through the heater at a predetermined temperature which is provided on the flow path over a predetermined length of time, thereby heating the mixed solution, letting the mixed solution after heating pass through the back-pressure generator, and then subjecting the mixed solution to the fluorometric detector to record the intensity of fluorescent light.

4. A method for separation analysis of reducing sugars using the apparatus according to 1 or 2 above, comprising loading the sample solution containing reducing sugars on an anion exchange resin column, washing the column by passing therethrough a sufficient volume of a first mobile phase which is an aqueous solution containing at least one basic amino acid at a predetermined concentration and boric acid at a predetermined concentration, supplying to the column continuously at a predetermined flow rate a second mobile phase which is a boric acid aqueous solution containing an elevated concentration of boric acid or water-soluble inorganic salt, as compared with the first mobile phase, to elute the reducing sugars, leading the eluate from the column continuously to a flow path, letting the eluate flow through the heater at a predetermined temperature which is provided on the flow path over a predetermined length of time, thereby heating the mixed solution, letting the mixed solution after heating pass through the back-pressure generator, and then subjecting the mixed solution to the fluorometric detector to record the intensity of fluorescent light.

5. The method according to 3 or 4 above, wherein the reducing sugars include mannose-6 phosphate.

Effect of the Invention

In the analysis of reducing sugars by the post-column fluorescence detection/boric acid complex anion exchange method, the present invention enables to enhance detection sensitivity by eliminating noises. Therefore, the apparatus, or the method, for separation analysis according to the present invention enables direct use of detection results, without need of rectifying them by any special software, thereby making not only simple but accurate detection possible.

DETAILED DESCRIPTION OF THE INVENTION

In the present invention, the term "boric acid aqueous solution" includes a solution which further contains a small amount of a base or basic salt as a pH adjusting agent, such as sodium hydroxide (or sodium borate) for adjusting the pH as needed.

In the present invention, the term "concentration of boric acid", when used in connection with a boric acid aqueous solution, means the concentration of boron in the aqueous solution calculated as boric acid ($H_3BO_3$). Therefore, the term also includes boric acid added in the form of a salt (e.g., sodium borate).

In the present invention, there is no particular limitation as to the conditions in performing the post-column fluorescence detection/boric acid complex anion exchange method as long as they allow separation and analysis of reducing sugars, including those described in the aforementioned literatures.

For example, the method can be conducted under the conditions shown in Tables 1 and 2 (methods I and II). In method I the concentration of an inorganic salt is increased over time, and so is the concentration of boric acid in method II. If M6P is included among the reducing sugars to be analyzed, method I shown in Table 1 or like methods can be employed particularly preferably for separation analysis of M6P.

TABLE 1

Conditions in post-column fluorescence detection/boric acid complex anion exchange method (Methods I and II)

|  | Method I | Method II |
|---|---|---|
| Method for detection (Fluorescence) | Excitation light 320 nm, Fluorescent light 430 nm | Excitation light 320 nm, Fluorescent light 430 nm |
| Solutions A | 100 mM boric acid (pH 9.0) | 100 mM boric acid (pH 8.0) |
| Solutions B | 100 mM boric acid, 200 mM NaCl (pH 9.0) | 400 mM boric acid (pH 9.0) |
| Flow rate of mobile phase | 0.3 mL/min | 0.6 mL/min |
| Column Temperature | 65° C. | 65° C. |
| Reagent solution for reaction | 1 w/v % boric acid, 3 w/v % dl-arginine | 1 w/v % boric acid, 3 w/v % dl-arginine |
| Injection speed of reagents solution for reaction | 0.2 mL/min | 0.5 mL/min |
| Temperature inside heater | 150° C. | 150° C. |

TABLE 2

Ratio of solution B in mobile phases and time when for the mobile phases are flown through the column

| Type of mobile phase | Method I | | Method II | |
|---|---|---|---|---|
|  | Time (min) | Solution B (v/v %) | Time (min) | Solution B (v/v %) |
| 1st Mobile phase | 0-35 | 10 | 0-5 | 0 |
| 2nd Mobile phase | 35-60 | 10→75 | 5-50 | 0→100 |
| 2nd Mobile phase | 60-70 | 100 | 50-70 | 100 |
| 1st Mobile phase | 70 and thereafter | 10 | 70 and thereafter | 0 |

Note:
The time when the sample loading is completed is taken as the reference time (0 minute).

In the present invention, solution A and solution B used as the mobile phase solutions either alone or in the form of their mixture, are both aqueous solutions. In raising the ratio of solution B, though the ratio may be raised either continuously or intermittently, it is preferably raised continuously, most preferably in a linear fashion (i.e., continuously and at a constant rate). The raising of the ratio of solution B may be carried out until the analyte reducing sugars have been eluted.

In the present invention, the term "first mobile phase" refers to the mobile phase which is employed first when starting the chromatography after the sample loading on the column is completed. The first mobile phase is an aqueous solution containing boric acid at a predetermined concentration and may contain a water-soluble inorganic salt at a predetermined concentration. The concentration of boric acid in the first mobile phase is preferably in the range of 50-150 mM. The concentration of water-soluble inorganic salt in the first mobile phase is preferably in a range of 0-30 mM. The term "second mobile phase" means the mobile phase which is passed through the column to elute the reducing sugars, after passage of the first mobile phase through the column, and contains an elevated concentration of boric acid of water-soluble inorganic salt, as compared with the first mobile phase (In table 2 above, the second mobile phase is a mobile phase in which the ratio of solution B is elevated). When referred to simply as "mobile phase", the term includes the first mobile phase and second mobile phase, without distinction.

In the present invention, when elevating the concentration of an inorganic salt in the mobile phase as performed in method I described above (sodium chloride in the case of method I), it is enough to elevate the salt concentration of the second mobile phase until it reaches around 200 mM. Though there is no particular limitation as to what inorganic salt is used here as far as it is a water-soluble inorganic salt (except a salt of boric acid, though), a neutral salt, which gives a neutral pH when dissolved in water, is preferred, and sodium chloride and potassium chloride are particularly preferred.

In the present invention, when elevating the concentration of an inorganic salt in the second mobile phase as performed in method I described above, though there is no particular limitation about the concentration of boric acid in the mobile phase as far as the analysis of reducing sugars, e.g., neutral reducing sugars or M6P, depending on the objective, is possible, the concentration is preferably 50-150 mM, more preferably 75-125 mM, and particularly preferably about 100 mM. In addition, pH of the mobile phase used here is preferably in the range of 7.5 to 9.5, and particularly preferably about 9.

In the present invention, when the concentration of boric acid is elevated in the second mobile phase as performed in method II described above, it is preferable to elevate the concentration of the boric acid in the mobile phase from 100 mM to 400 mM, through the range may be changed as desired according to the type of reducing sugars to be analyzed. In addition, the pH of solution A that is employed here is preferably in the range of 7.5 to 8.5, and particularly preferably about 8, and the pH of solution B is preferably in the range of 8.5 to 9.5, and particularly preferably about 9.

The flow rate of the mobile phase should be appropriately adjusted according to the analytical equipment employed and the type of reducing sugars to be analyzed so that a good analytical result may be obtained. In general the flow rate is adjusted to 0.1 to 1 mL/min, though it may be adjusted to less than 0.1 mL/min or more than 1 mL/min, depending, e.g., on the characteristics of the analytical instrument.

The anion exchanger resin employed in the anion exchanger column chromatography in the present invention may be a weak anion exchanger resin or a strong anion exchanger resin, though a strong anion exchanger resin is preferably employed. Though elution from an anion exchanger column may be carried out at room temperature, it is preferably carried out while heating the column in an oven or the like. When heating the column, however, the temperature should not exceed about 70° C., and preferably it is set at about 65° C.

The basic amino acids used in the present invention, though there is no particular limitation, are preferably arginine, lysine or histidine, and arginine is particularly preferred. While one of basic amino acids may be employed alone, two or more basic amino acids may also be employed in a mixture. Further, the basic amino acid used therein may be added by injection in the form of a reagent solution, i.e., an aqueous solution containing the same, into the eluate flowing through the flow path out of the column. The injection speed of a basic amino acid may be set as desired insofar as the speed is kept constant during a single round of analysis. In general, such injection may be performed so that its concentration (final concentration) after mixing with the eluate from the column in the flow path may become 0.1-2 w/v %, preferably 0.5-1.8 w/v %, and more preferably 1.0-1.5 w/v %. Addition of a basic amino acid is performed preferably, for example, by injection in the form of a boric acid aqueous solution containing the basic amino acid. In such a case, the concentration of boric acid in the aqueous solution may be adjusted to be equal to the boric acid concentration in the mobile phase, though it may be allowed that its concentrations differ from each other to some extent. Alternatively, a basic amino acid, instead of being injected later into the flow path in the form of a reagent solution, may be included and dissolved in advance in the mobile phase at a predetermined concentration. In this case, a supply channel, which is necessary if a reagent solution is later added which contains a basic amino acids to the eluate, may be eliminated. And in this case, the concentration of amino acid in the mobile phase may be adjusted to 0.1-2 w/v %, preferably 0.5-1.8 w/v %, and more preferably 1.0-1.5 w/v %.

In the present invention, the reaction temperature at which the reaction is allowed to proceed between reducing sugars and a basic amino acid contained in the eluate from the column (the eluate after the addition of the basic amino acid where a basic amino acid is added to the eluate from the column) by heat (heat reaction) may be set at 140-180° C., and preferably at about 150° C. The reaction taking place here is the Maillard reaction, in which the reducing group of the reducing sugars reacts with a basic amino acid to form a brown substance (melanoidine). The heater is a device having a heating zone for heating the solution in the flow path for a predetermined length of time up to a predetermined temperature, and any heater having such a heating zone may be used without particular limitation. The length of time of heating within the heater, though there is no particular limitation if it is sufficient to let the Maillard reaction proceed, is generally 1 to 20 minutes.

In the present invention, to further reduce noises in the fluorescence detected by fluorometric detector, the eluate after the heat reaction is preferably cooled down by being passed through a cooling device. Though there is no particular limitation insofar as it would cause no trouble in subsequent measurement of fluorescence intensity, the temperature of eluate after cooling down is preferably 15 to 70° C. This cooling may be performed, e.g., by air cooling or water cooling the flow path with a cooling device. Air cooling, for example, may be performed by blowing the flow path with a fan. In the case of water cooling, tap water may be used directly. Alternatively, for example, the eluate after heat reaction may be cooled down to a temperature in the column oven by passing the flow path through a cooling bath (5 in FIG. 1).

A back-pressure generator used in the present invention is installed in a flow path to increase the pressure of the solution in the flow path on the upstream side of it (back pressure). The back-pressure generator has the effect to reduce noises in the fluorescence detected by the fluorometric detector in the post-column detection method. Any sort of back-pressure generator may be employed without particular limitation as long as it can generate a back pressure. Back pressure, for example, can be generated by narrowing the flow path inside the back-pressure generator. A back-pressure regulator on the market [1/16. flange-type unit (4×1.3 cm), mfd. by SSI, and BACK PRESSURE REGULATOR ASSEMBLY, WITH P-763 (100 PSI) CARTRIDGE, No U-607, mfd. by Upchurch Scientific] can be suitably used as a back-pressure generator in the present invention. These back-pressure regulators are devices generally used as a device to be attached to a detector exit to generate a constant back pressure in the detector.

In the present invention, a back-pressure generator is installed in the flow path between a heater and a fluorometric detector. When a cooling device is installed downstream of the heater, a back-pressure generator is placed preferably downstream of the cooling device.

The sugars that can be analyzed according to the present invention are such reducing sugars that undergo the Maillard reaction with basic amino acids. Examples of them include monosaccharides such as glucose, mannose, galactose, fructose, rhamnose, fucose and the like; oligosaccharides such as maltose, maltotriose and the like; amino sugars such as glucosamine, galactosamine and the like, uronic acid such as glucuronic acid; and phosphated saccharides such as mannose-6-phosphate, and in particular, monosaccharides such as mannose, galactose and fucose; and phosphated sugars such as mannose-6-phosphate. Sugars to be analyzed are prepared in the form of a sample solution, i.e., a solution obtained by dissolving them in a desired medium at desired concentrations. The medium used here is an aqueous medium, and preferably pure water or a solution of the same composition as the first mobile phase.

EXAMPLES

Though the present invention will be described in further detail below with reference to examples, it is not intended that the present invention be limited to those examples.
[Preparation of Standard Solution]
Three hundred mg of D(+)-mannose, 100 mg of L(−)-fucose, and 300 mg of D(+)-galactose were dissolved in purified water to make 100-mL of solution. This solution was diluted 20-fold with purified water and the diluted solution was used as the neutral reducing sugar mixture standard solution. Ten mg of sodium mannose-6-phosphate was dissolved in water to make a 5 mL of solution and this was used as the M6P standard solution. Eighteen mL of the neutral reducing sugar mixture standard solution and 2.5 mL of the M6P standard solution were mixed and were used as the reducing sugar standard solution.
[Preparation of Solutions for Mobile Phases]
To purified water was added 6.2 g of boric acid and dissolved, and after adjusting the pH to 9.0 with 2N sodium hydroxide, purified water was added to make a total volume of 1000 mL, which then was suction-filtered through a 0.22 μm membrane filter. The solution thus obtained was designated solution A (100 mM boric acid solution (pH 9.0)). To purified water were added 6.2 g of boric acid and 11.7 g of sodium chloride and dissolved, and after adjusting the pH to 9.0 with 2N sodium hydroxide, purified water was added to make a total volume of 1000 mL, which then was suction-filtered through a 0.22 μm membrane filter. The solution thus obtained was designated solution B (100 mM boric acid-200 mM sodium chloride solution (pH 9.0)).
[Preparation of Reagent Solution]
To purified water were added 30 g of L-arginine and 10 g of boric acid and dissolved, the total volume was adjusted to 1000 mL, and the solution was suction-filtered through a membrane filter with the pore size of not more than 0.22 μm, and the solution thus obtained was used as the reagent solution.

Example 1

Analysis of Sugars by Post-Column fluorescence Detection/Boric Acid Complex Anion Exchange Method (1) Apparatus
An anion exchanger column, Shim-pack ISA-07/52504 (4.0 mm I.D.×250 mm, base material: polystyrene gel, stationary phase: quaternary ammonium group, Shimazu Corp.) was attached to Shimazu HPLC System LC-10Avp (reducing sugar analysis system), and further, Shim-pack guard column ISA (4.0 mm I.D.×50 mm, Shimazu Corp.) was set as a column oven for heating the column. A Heat Block (ALB-221, mfd. by Asahi Techno Glass) was set downstream of the column outlet as a heater. The column was heated at 65° C. in the column oven, and the heater was set at 150° C. A cooling bath (a bath filled with tap water at room temperature) was installed downstream of the Heat Block, downstream of which was installed a back-pressure regulator (M&S Instruments Inc., U-167) as a back-pressure generator. A fluorometric detection system was installed further downstream of this and adjusted so that it would irradiate excitation light at the wavelength of 320 nm and detect fluorescent light at the wavelength of 430 nm. The arrangement of the apparatus and the flow paths are illustrated in FIG. 1.

(2) Operation Procedures

Figure 1:
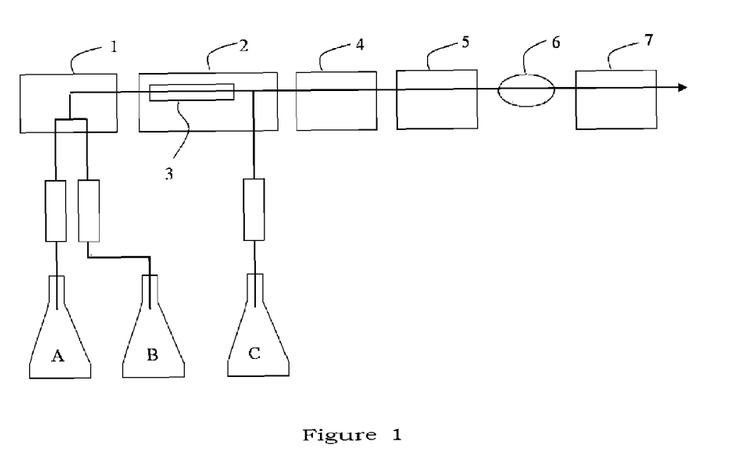
FIG. 1 A diagram schematically illustrating the arrangement of apparatus and flow path in the examples.

Solutions A and B were set on the autosampler of the reducing sugar analysis system, and the reagent solution was set so as to be supplied downstream of the column outlet (upstream of the Heat Block) (See FIG. 1). After the column was equilibrated with the first mobile phase prepared by mixing solution A and solution B at a volume ratio of 90:10 (thus, containing 100 mM boric acid and 20 mM sodium chloride), the reducing sugar standard solution was loaded onto the column.

After the columns was loaded with the reducing sugar standard solution, the first mobile phase was allowed to flow through the column at the flow rate of 0.3 mL/min for 35 min, and then the volume ratio between solution A and solution B was changed in a linear fashion to 25:75 over 25 min at the same flow rate (thus, containing 100 mM boric acid, while sodium chloride being increased up to 150 mM), and further the volume ratio of solution B was set at 100% (thus, containing 100 mM boric acid and 200 mM sodium chloride) and the solution was allowed to flow at the same flow rate for 10 min, and then solution A and solution B were allowed to flow at a volume ratio of 90:10 (thus, containing 100 mM boric acid and 20 mM sodium chloride) as was the case of the first mobile phase. The reagent solution was supplied to the flow path so as to mix with the eluate from the column in the downstream of the column outlet, at a flow rate of 0.2 mL/min. Thus, the concentration of arginine in the reaction mixture solution was 3×0.2/(0.3+0.2)=1.2 w/v %. Table 3 shows the conditions in the post-column fluorescence detection/boric acid complex anion exchange method used there.

TABLE 3

Terms and conditions in post-column fluorescence detection-boric acid complex anion exchange method (example)

| Method for detection (Fluorescence) | Excitation light 320 nm, Fluorescent light 430 nm |
|---|---|
| Solutions A | 100 mM boric acid (pH 9.0) |
| Solutions B | 100 mM boric acid, 200 mM NaCl (pH 9.0) |
| Flow rate of mobile phases | 0.3 mL/min |
| Column Temperature | 65° C. |
| Reagent solution | 1 w/v % boric acid, 3 w/v % dl-arginine |
| Injection speed of reagent solution | 0.2 mL/min |
| Temperature in heater | 150° C. |

Comparative Example 1

Analysis of Sugars by Post-Column Fluorescence Detection/Boric Acid Complex Anion Exchange Method Except that it did not use a back-pressure generator, the reducing sugar standard solution was analyzed on the same apparatus following the same operating procedure as described in Example 1 above.

[Evaluation of Results Derived from the Analysis]

Figure 2:
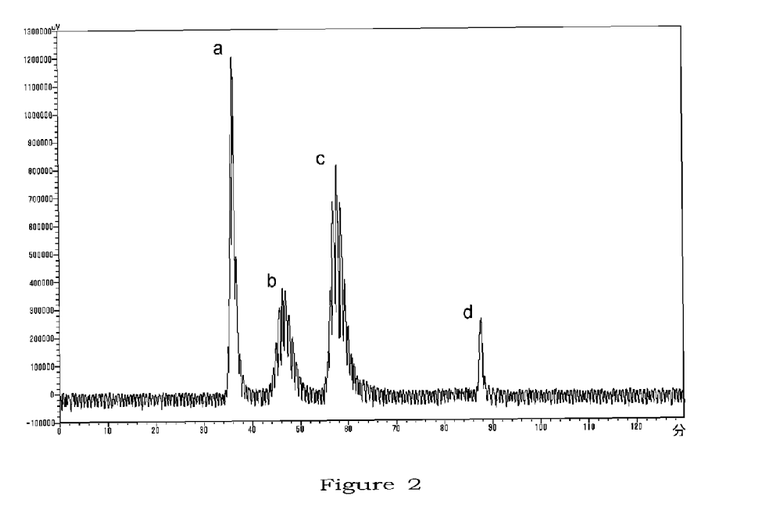
FIG. 2 A chromatogram showing the result of analysis of a reducing sugar standard solution when no back-pressure generator was installed. The vertical axis represents fluorescence intensity, and the horizontal axis represents time (in minutes) that lapsed after completion of loading the reducing sugar standard solution. Peaks "a" to "d" represent, a:mannose, b:fucose, c:galactose, and d:M6P, respectively.
Figure 3:
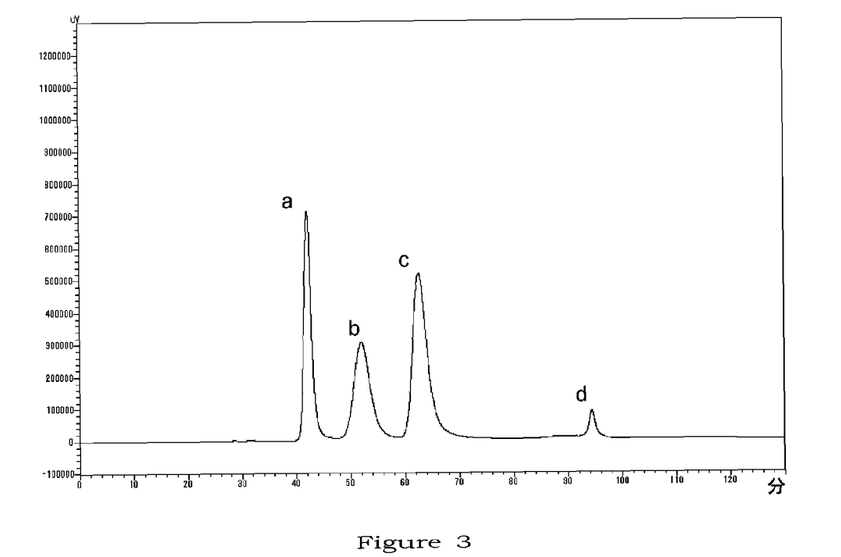
FIG. 3 A chromatogram (1) showing the result of analysis of the reducing sugar standard solution when a back-pressure generator was installed. Ditto about the horizontal axis, vertical axis, and peaks "a" to "d". The water-soluble inorganic salt used for preparation of solution B is sodium chloride.
Figure 4:
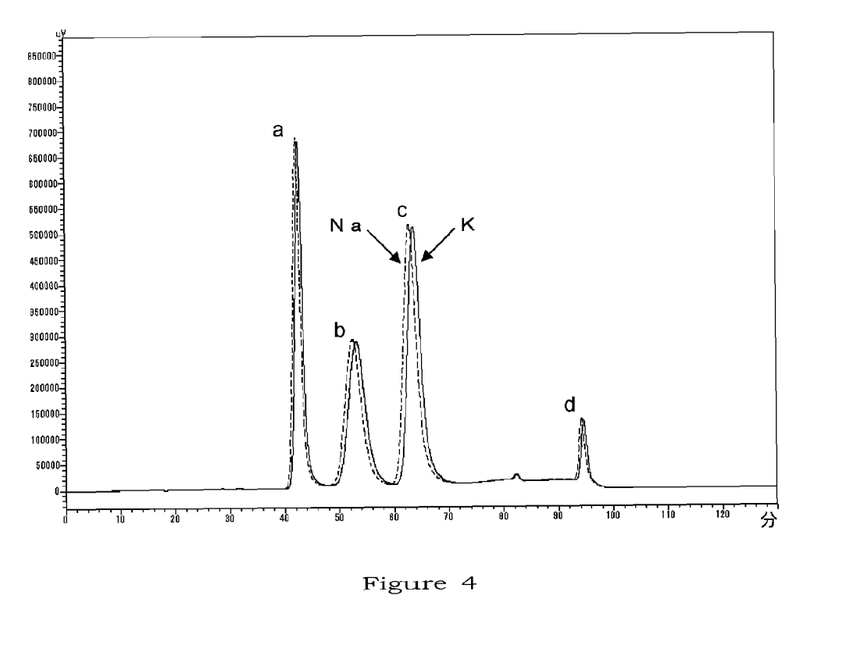
FIG. 4 Chromatograms (2) showing the result of analysis of the reducing sugar standard solution when a back-pressure generator was installed. Ditto about the horizontal axis, vertical axis, and peaks "a" to "d". The water-soluble inorganic salts used for preparation of solution B were sodium chloride (Na: broken line) and potassium chloride (K: solid line).

The result of analysis of reducing sugar standard solution carried out with no back-pressure generator installed [i.e., the result of analysis in Comparative Example above] was found to contain noises in the measurement curve produced from the fluorescence detected with the fluorometric detector, and the level of the noises was such that it would hinder accurate calculation of the area (AUC) of each peak (FIG. 2). On the other hand, with a back-pressure generator installed, the result of analysis obtained [i.e., the result of analysis obtained in Example 1 above], exhibited a smooth curve which was free of noises to such an extent that the area (AUC) of each peak can be accurately calculated (FIG. 3).

Example 2

Analysis of Sugars by Post-Column Fluorescence Detection/Boric Acid Complex Anion Exchange Method Under the same condition as in Example 1, the reducing sugar standard solution was analyzed. Then, under the same condition as in Example 1 except that solution B was prepared using 200 mM of potassium chloride, instead of 200 mM of sodium chloride, as the inorganic salt contained in solution B, the reducing sugar standard solution was analyzed, and the both results were compared.

With a back-pressure generator installed, when the inorganic salt contained in solution B, 200 mM of sodium chloride, was replaced with 200 mM of potassium chloride, a smooth curve was also obtained which was free of noises to such an extent that the area (AUC) of each peak can be accurately calculated as in the case where 200 mM of sodium chloride was used.

INDUSTRIAL APPLICABILITY

The present invention can be used as an apparatus for high sensitivity analysis of reducing sugars in the post-column fluorescence detection/boric acid complex anion exchange method, as it removes noises in fluorescence detected by a fluorometric detector

[Description of Signs]

| 1: | Autosampler |
|---|---|
| 2: | Column oven |
| 3: | Column |
| 4: | Heater (Heat Block) |
| 5: | Cooling bath |
| 6: | Back-pressure generator |
| 7: | Fluorometric detector |
| A: | Solution A |
| B: | Solution B |
| C: | Reagents solution |

The invention claimed is:

1. An apparatus for separation analysis of reducing sugars including mannose-6 phosphate contained in a sample solution using column chromatography, comprising an anion exchange resin column for separation of reducing sugars contained in the sample solution, a heater for causing reducing sugars contained in an eluate from the column to react with basic amino acid, a fluorometric detector for measuring the intensity of fluorescence emitted from the eluate under continuous irradiation with excitation light after the reaction in the heater, a back-pressure generator present between the heater and the fluorometric detector.

2. The apparatus for separation analysis of reducing sugars according to claim 1, wherein a cooling device is present between the heater and the back-pressure generator.

3. A method for separation analysis of reducing sugars using an apparatus for separation analysis of reducing sugars contained in a sample solution using column chromatography, comprising an anion exchange resin column for separation of reducing sugars contained in the sample solution, a heater for causing reducing sugars contained in an eluate from the column to react with basic amino acid, a fluorometric detector for measuring the intensity of fluorescence emitted from the eluate under continuous irradiation with excitation light after the reaction in the heater, a back-pressure generator present between the heater and the fluorometric detector, wherein the method comprises,
    loading the sample solution containing reducing sugars on an anion exchange resin column,
    washing the column by passing therethrough a first mobile phase which is an aqueous solution containing boric acid at a predetermined concentration,
    supplying to the column continuously at a predetermined flow rate a second mobile phase which is a boric acid aqueous solution containing an elevated concentration of water-soluble inorganic salt, as compared with the first mobile phase to elute the reducing sugars,
    leading the eluate from the column continuously to a flow path,
    continuously adding at least one basic amino acid at a predetermined rate to the eluate,
    letting the eluate containing the basic amino acid added thereto flow through the heater at a predetermined temperature which is provided on the flow path over a predetermined length of time, thereby heating the mixed solution,
    letting the mixed solution after heating pass through the back-pressure generator, and then
    subjecting the mixed solution to the fluorometric detector to record the intensity of fluorescent light,
    wherein the water-soluble inorganic salt is sodium chloride or potassium chloride.

4. A method for separation analysis of reducing sugars using an apparatus for separation analysis of reducing sugars contained in a sample solution using column chromatography, comprising an anion exchange resin column for separation of reducing sugars contained in the sample solution, a heater for causing reducing sugars contained in an eluate from the column to react with basic amino acid, a fluorometric detector for measuring the intensity of fluorescence emitted from the eluate under continuous irradiation with excitation light after the reaction in the heater, a back-pressure generator present between the heater and the fluorometric detector, wherein the method comprises,
    loading the sample solution containing reducing sugars on an anion exchange resin column,
    washing the column by passing therethrough a first mobile phase which is an aqueous solution containing boric acid at a predetermined concentration,
    supplying to the column continuously at a predetermined flow rate a second mobile phase which is a boric acid aqueous solution containing an elevated concentration of water-soluble inorganic salt, as compared with the first mobile phase to elute the reducing sugars,
    leading the eluate from the column continuously to a flow path,
    continuously adding at least one basic amino acid at a predetermined rate to the eluate,
    letting the eluate containing the basic amino acid added thereto flow through the heater at a predetermined temperature which is provided on the flow path over a predetermined length of time, thereby heating the mixed solution,
    letting the mixed solution after heating pass through the back-pressure generator, and then
    subjecting the mixed solution to the fluorometric detector to record the intensity of fluorescent light,
    wherein the concentration of the water-soluble inorganic salt of the second mobile phase is elevated until it reaches around 200 mM.

5. A method for separation analysis of reducing sugars using an apparatus for separation analysis of reducing sugars contained in a sample solution using column chromatography, comprising an anion exchange resin column for separation of reducing sugars contained in the sample solution, a heater for causing reducing sugars contained in an eluate from the column to react with basic amino acid, a fluorometric detector for measuring the intensity of fluorescence emitted from the eluate under continuous irradiation with excitation light after the reaction in the heater, a back-pressure generator present between the heater and the fluorometric detector, wherein the method comprises,
    loading the sample solution containing reducing sugars on an anion exchange resin column,
    washing the column by passing therethrough a first mobile phase which is an aqueous solution containing at least one basic amino acid at a predetermined concentration and boric acid at a predetermined concentration,
    supplying to the column continuously at a predetermined flow rate a second mobile phase which is a boric acid aqueous solution containing an elevated concentration of water-soluble inorganic salt, as compared with the first mobile phase, to elute the reducing sugars,
    leading the eluate from the column continuously to a flow path,
    letting the eluate flow through the heater at a predetermined temperature which is provided on the flow path over a predetermined length of time, thereby heating the mixed solution,
    letting the mixed solution after heating pass through the back-pressure generator, and then
    subjecting the mixed solution to the fluorometric detector to record the intensity of fluorescent light,
    wherein the water-soluble inorganic salt is sodium chloride or potassium chloride.

6. A method for separation analysis of reducing sugars using an apparatus for separation analysis of reducing sugars contained in a sample solution using column chromatography, comprising an anion exchange resin column for separation of reducing sugars contained in the sample solution, a heater for causing reducing sugars contained in an eluate from the column to react with basic amino acid, a fluorometric detector for measuring the intensity of fluorescence emitted from the eluate under continuous irradiation with excitation light after the reaction in the heater, a back-pressure generator present between the heater and the fluorometric detector, wherein the method comprises,
    loading the sample solution containing reducing sugars on an anion exchange resin column,
    washing the column by passing therethrough a first mobile phase which is an aqueous solution containing at least one basic amino acid at a predetermined concentration and boric acid at a predetermined concentration, supplying to the column continuously at a predetermined flow rate a second mobile phase which is a boric acid aqueous solution containing an elevated concentration of water-soluble inorganic salt, as compared with the first mobile phase, to elute the reducing sugars, leading the eluate from the column continuously to a flow path, letting the eluate flow through the heater at a predetermined temperature which is provided on the flow path over a predetermined length of time, thereby heating the mixed solution, letting the mixed solution after heating pass through the back-pressure generator, and then subjecting the mixed solution to the fluorometric detector to record the intensity of fluorescent light, wherein the concentration of the water-soluble inorganic salt of the second mobile is elevated until it reaches around 200 mM.

* * * * *